(12) United States Patent
Händel

(10) Patent No.: US 6,886,420 B2
(45) Date of Patent: May 3, 2005

(54) SAMPLING APPARATUS

(75) Inventor: Elmar Händel, Siegburg (DE)

(73) Assignee: RHE Haendel Engineering GmbH & Co KG (DE)

(*) Notice: Subject to any disclaimer, the term of this patent is extended or adjusted under 35 U.S.C. 154(b) by 230 days.

(21) Appl. No.: 10/061,905

(22) Filed: Feb. 1, 2002

(65) Prior Publication Data
US 2002/0166392 A1 Nov. 14, 2002

(30) Foreign Application Priority Data

Feb. 1, 2001 (DE) .................................. 201 01 741 U
Feb. 8, 2001 (DE) .................................. 201 02 308 U

(51) Int. Cl.[7] .............................. G01N 1/10; G01N 1/22
(52) U.S. Cl. .............................. 73/863.85; 73/863.83
(58) Field of Search .................... 73/863.81–863.86, 73/863.53, 863.54, 863.578, 863.57

(56) References Cited

U.S. PATENT DOCUMENTS

| 2,786,355 A | * | 3/1957 | Day et al. ................. 73/863.81 |
| 3,864,978 A | * | 2/1975 | Stephens ................. 73/863.84 |
| 3,868,854 A | * | 3/1975 | Trever et al. ............. 73/863.85 |
| 4,128,008 A | * | 12/1978 | Linenberg ................ 73/863.12 |
| 4,147,062 A | * | 4/1979 | Jaeger ...................... 73/763.83 |
| 4,262,534 A | * | 4/1981 | Morrison ................. 73/863.86 |
| 4,269,064 A | * | 5/1981 | Johnson et al. .......... 73/863.82 |
| 4,548,088 A | * | 10/1985 | Hood, Jr. ................. 73/864.34 |
| 4,562,747 A | * | 1/1986 | Jaeger ..................... 73/863.54 |
| 4,630,479 A | * | 12/1986 | Wagener et al. ......... 73/863.83 |
| 5,463,908 A | * | 11/1995 | Rosolia .................... 73/863.83 |
| 5,585,576 A | * | 12/1996 | Jaeger ..................... 73/863.85 |
| 6,055,870 A | * | 5/2000 | Jaeger ..................... 73/863.83 |

FOREIGN PATENT DOCUMENTS

| CA | 11 88131 | * | 6/1985 | ............ G01N/1/10 |
| DE | 4316734 A1 | * | 12/1993 | ............ G01N/1/13 |
| DE | 29723361 U1 | * | 12/1998 | ............ G01N/1/20 |
| EP | 214903 A1 | * | 3/1987 | ............ 73/863.41 |
| EP | 575916 A2 | * | 12/1993 | ............ A61B/5/14 |
| EP | 724145 A2 | * | 7/1996 | ............ G01N/1/20 |
| EP | 754491 A1 | * | 1/1997 | ............ B01F/15/04 |
| WO | WO 84/04591 A1 | * | 11/1984 | ............ G01N/1/20 |

OTHER PUBLICATIONS

Derwent –Acc–Nui: 1980–C9149C "Liquid Sample Extraction Chamber–has no Coupled to Plate Valve External Casins and Sprung via Mounting Disc, with Piston for Sampling".*
Abstract of SU 675338 A Nikolaeus et al., Jul. 19, 1979.*
Derwent–Acc–Nui 1993–166022 "Device for Deep Level Sampling of Water–Sample is Drawn and Transferred to Bottle by Reciprocating Plunger with Sampling Recess".*
Abstract & Clipped Image of SU 1737313 A1 Lebedeu et al, May 1992.*

* cited by examiner

Primary Examiner—Thomas P. Noland
(74) Attorney, Agent, or Firm—Locke Liddell & Sapp LLP

(57) ABSTRACT

An apparatus for extracting samples of product such as liquid or gas from a product chamber. The apparatus comprises a sample chamber arranged in a housing for movement between positions projected into and retracted from the product chamber. The housing is connected to a lateral side of the product chamber in such a manner as to surround an opening thereof in a sealing relation. The apparatus further has a product outlet and a plunger that includes the sample chamber and is supported for axial movement in the housing which is configured as a cylinder.

17 Claims, 2 Drawing Sheets

SAMPLING APPARATUS

The present invention relates to an apparatus for extracting samples of product such as a liquid or a gas from a product chamber, said apparatus comprising a sample chamber arranged in a housing for movement between positions projected into and retracted from the product chamber, said housing being connected to a lateral side of the product chamber in such a manner as to surround an opening thereof in a sealing relation, and further comprising a product outlet and a plunger that includes the sample chamber and is supported for axial movement in said housing which is configured as a cylinder.

BACKGROUND OF THE INVENTION

It is known from prior art that certain manufacturing operations require samples of product to be retracted from product chambers for monitoring the manufacturing process and in particular for checking the resulting product from time to time.

DE 43 16 734 A1 for example discloses an apparatus of this type for extracting a sample of product, said apparatus comprising a sample chamber arranged in a housing for movement between a position projected into the product chamber and a position retracted from the product chamber, which housing is connected to a lateral side of the product chamber in such a manner that it surrounds an opening thereof in a sealing relation, and comprising a product outlet in said housing. This type of apparatus is concerned with a sampling valve for extracting liquid or relatively fluent substances from vessels or pipelines. This pre-known sampling valve is comprised of a valve body having an inlet and an outlet which are separated from each other by means of a plunger arrangement. Charging of the medium is effected by extending one of said plungers, the other one of said plungers being moved along by said first plunger during the extension thereof to a position in which the outlet is closed. Accordingly, this sampling valve has an axially movable displacement plunger that extends from the inlet to the outlet. This displacement plunger is followed by a shut-off plunger, and by the relative movement of these plungers a receiving chamber can be formed there between, and in the course of this relative movement said shut-off plunger can be transferred by means of a catch device on the displacement plunger to a position in which the outlet is closed. Accordingly, it is the relative movement between these two plungers which is important. However, for diverse samples of product this technique is not desired. In addition, it can be seen that the correct operation of this pre-known sampling valve is governed by its fitting position, because the sample of product to be extracted is required to flow automatically into the receiving chamber formed between the displacement plunger and the shut-off plunger. Particularly in the case of viscous media it may happen that amounts are extracted which do not correspond to exactly measured amounts as the same are required for sample analysis.

WO 84/04591, too discloses an apparatus for extracting a sample of product from a product chamber. However, in this pre-known device the sample chamber is configured as a continuous bore which is not suited for extracting all kinds of samples of product. Moreover, in this apparatus, too the sample chamber must be fitted in a particular position in order that a measured amount of sample of product can be extracted. Hence, this type of apparatus serves for measuring permeability.

Further, from EP 0 724 145 A2 are known a method or apparatus for filtrate measuring. To this end the apparatus comprises two plungers and a plunger rod, both plungers being movable relative to each other. The chamber which is arranged between these two plungers and which is variable is projected into a tube in which a substance to be measured flows. By retracting both plungers, which are moved relatively to each other, from the tube the sample of product is extracted, so that a filtrate is supplied to a filtrate storage tank in which the required measurements are made. Thereafter, the filtrate is returned to the pipeline. A similar apparatus is also known from EP 0 754 941 A1.

Another sampling valve is described in U.S. Pat. No. 5,585,576. In this sampling valve the sample chamber is arranged between a seal and a cutter means. Said seal and said cutter means are mounted and spaced from each other on a movable axis.

Finally, DE 297 23 631 U1 discloses another well tried apparatus for extracting a sample of product from a product chamber, wherein said sample of product is extracted by means of a sample chamber arranged in a housing and movable within said housing between positions projected into and retracted from the product chamber. In this apparatus the housing rests against a lateral side of the product chamber, surrounding an opening thereof in a sealing relation. The housing also has a product outlet. The sample chamber is arranged in a plunger which is supported for axial movement within said housing configured as a cylinder. Finally, the sample chamber is provided in the form of a diameter reduction of the plunger.

Basing on the above-described prior art an object of the present invention is to improve a sampling apparatus of this type to the effect that representative samples of product can be retracted from a product chamber in a simple and inexpensive manner, with an adequate sealing being provided between the product outlet and said product chamber and the danger of pollution of the sample chamber being as little as possible.

The solution of this problem provides that during normal operation the sample chamber is in its position projected into the product chamber and is movable toward the product outlet area only for the purpose of retracting the sample of product, and that the piston is sealed against the housing between the product outlet and the end of the housing protruding into the product chamber, by means of a sealing ring and preferably an O-ring.

Accordingly, the sampling apparatus of the invention is improved over prior art to the extent that during normal operation the sample chamber within the product chamber is constantly traversed by a flow of the product to be extracted, in particular by a liquid, whereby it is guaranteed that a representative sample is retracted at any time during the sampling. It is prevented, for example, that a sample of product is retracted which for reasons of time has already experienced alterations due to storage thereof in the sample chamber for an extended period of time already. Since there is a constant flow of the product to be retracted through the sample chamber, no material will adhere to it. Also, any medium remaining in the sample chamber after sampling is unable to bond, bake and/or adhere to sample chamber within the time in which the sample chamber is not inserted in the product chamber, since this period is set extremely short by the fact that the sample chamber is retracted from the product chamber only for the purpose of sampling and is returned to the product chamber as soon as the sample of product has been collected. Important in this context is the sealing ring which allows to obtain a sealing of the product chamber against the product outlet, so that the product can neither escape via the product outlet nor gaseous or liquid surrounding media enter into the product chamber.

According to another feature of the invention it is provided that the sealing ring is inserted in a recess in the inner lateral side of the housing. This configuration guarantees that the sealing ring is always present where it is needed and provides for a sufficient sealing effect between the plunger and the housing.

According to still another feature of the invention it is provided that the housing has a recess in the region of the sample chamber in its projected position. This recess serves for receiving the product during sampling. In this context it turned out to be advantageous if the said recess is formed as bore, of which the diameter is slightly smaller than the length of the sample chamber, so that the sample chamber can be rapidly and completely charged via said recess.

In particular, said bore is formed as a continuous bore so as to have access openings on both sides of the sample chamber allowing in case that the sample chamber is traversed by the product flow.

An advantageous further development of the apparatus according to the invention provides that the piston on the free end thereof in the region of the sample chamber has a sealing ring that is preferably configured as an O-ring. With this configuration the apparatus is also suited for very mobile media like solvents, for example, when the same are under high pressure. The additional sealing ring additionally seals the product outlet against the product chamber, so that even during sampling with the sample chamber arranged in the area of the product outlet any additional product can neither penetrate from the product chamber nor foreign matter enter the product chamber. This is particularly important when a fixed amount of sample of product is to be retracted at every sampling action.

Preferably, said sealing ring is inserted in a recess in the plunger, so that it provides for smooth sealing against the housing in any position of the plunger.

According to another feature of the invention a cup holder for receiving non returnable cups is detachably mounted to the product outlet. These non returnable cups offer the possibility of retracting samples of product rapidly and easily, a fresh cup being used for every sampling action in order to avoid the collected sample of product from being impaired and above all from being polluted.

Finally, an improvement of the apparatus according to the invention provides for the product outlet and cup holder to be connectable to each other via a bayonet catch in order to simplify and shorten the working steps necessary for sampling and for the subsequent preparation of the apparatus for new sampling.

BRIEF DESCRIPTION OF THE DRAWINGS

Further features and advantages of the invention will become apparent from the following description of the drawing showing a preferred embodiment of the sampling apparatus according to the present invention. In the drawing is shown by.

DETAILED DESCRIPTION OF THE INVENTION

Figure 1:
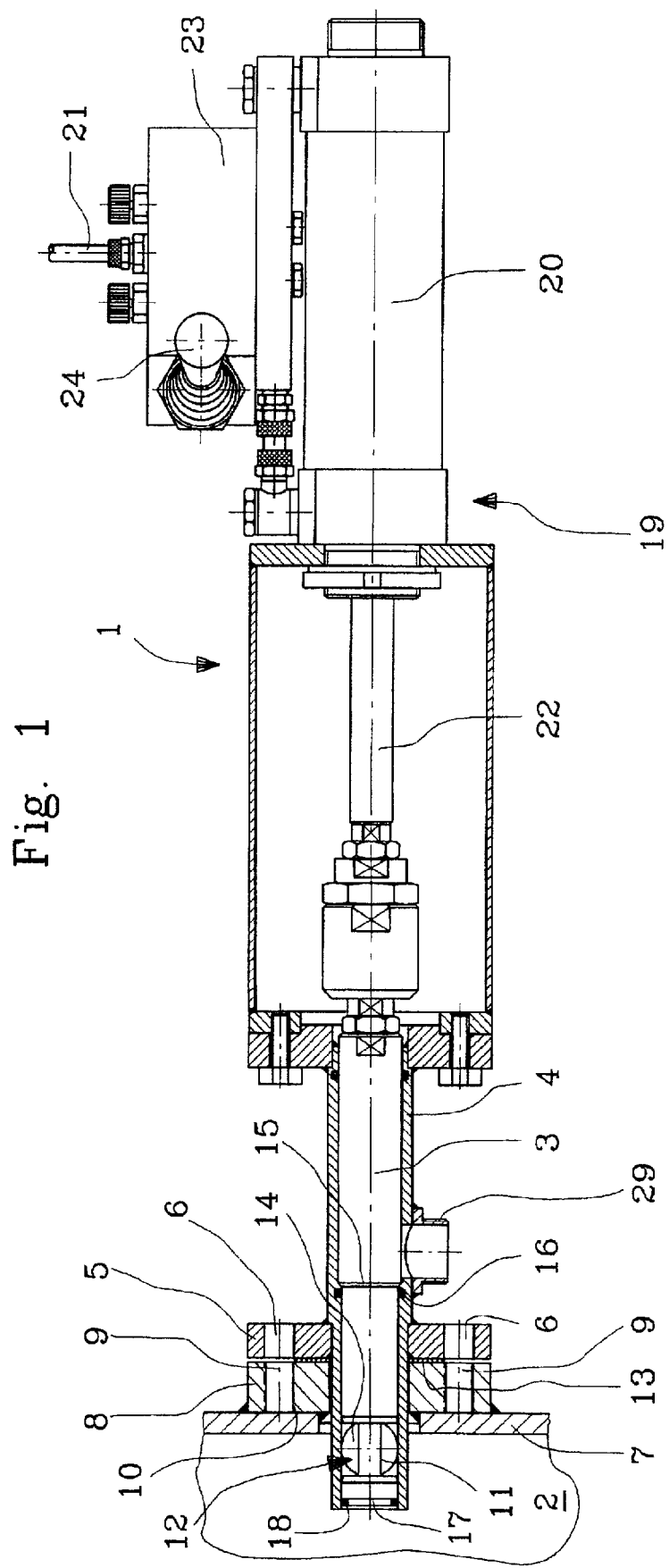
FIG. 1 a lateral sectional view of an apparatus for retracting a sample of product from a product chamber in a home position, and FIG. 2 the apparatus according to FIG. 1 in a sample retracting position.
Figure 2:
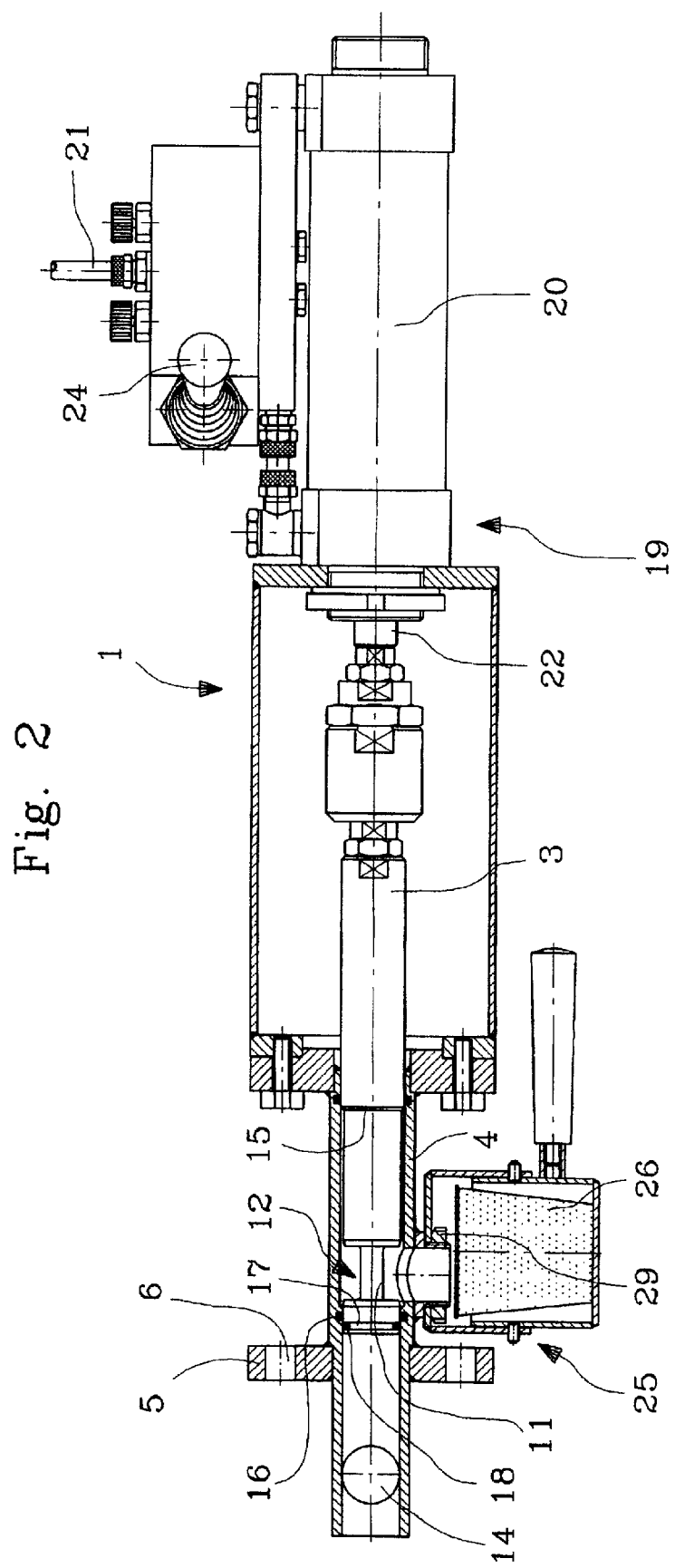

An apparatus 1 as shown by FIGS. 1 and 2 for retracting a sample of product from a product chamber 2, e.g. a liquid or a gas, is comprised of a plunger 3 arranged for axial movement within a hollow-cylindrical housing 4. Said housing 4 includes a flanged plate 5 which has a circular shape and includes several equally spaced bores 6 that are distributed over the ring area and serve for receiving screws (not further shown).

The housing 4 is inserted in a bore of a lateral side 7 of the product chamber in a sealing relation. In the region of this bore a flanged plate 8 is welded onto lateral side 7, said flanged plate 8 being annular in shape, so that a bore provided in said flanged plate 8 extends co-axially with the bore in said lateral side 7. Said bore in said flanged plate is penetrated by the housing 4. In this condition, the flanged plate 5 rests against the flanged plate 8, and the bores 6 of the flanged plate 5 are brought in registration with bores 9 in the flanged plate 8.

Between said flanged plate 5 and said flanged plate 8 a sealing 13 is provided.

The bores 9 have internal threads 10 adapted to receive machine screws passing through the bores of the flanged plate 5, so that the flanged plate 5 can be tightly screwed up with the flanged plate 8.

The plunger 3 has in its front portion a diameter reduction 11 and rests against the inner lateral surface of the housing 4 substantially with its outer lateral surface. Accordingly, a sample chamber 12 is formed in the region of the diameter reduction 11 which is circular in cross-section.

On its end inside the product chamber 2 said housing 4 has a bore 13, of which the diameter substantially corresponds to the length of the sample chamber 12. In the home position shown by FIG. 1, the plunger 3 is projected as far as possible into the housing 4, with the sample chamber 12 being arranged in the region of the bore 14.

It can be seen that the plunger 3 has a diameter enlargement 15 in its middle portion which, together with a corresponding edge inside the housing 4, is configured as a metallic sealing edge and performs a sealing function in the home position according to FIG. 1.

On the inner lateral surface of the housing 4 a continuous recess having a square cross-section is provided having inserted therein a sealing ring 16 in the form of an O-ring. This sealing ring 16 is positioned between a product outlet 29, which outlet joins said housing 4 in a flange-like fashion at right angles, and the end of the housing 4 engaging said product chamber 2. Said sealing ring 16 serves for additionally sealing the plunger 3 against the housing 4.

Furthermore, said plunger 3 is provided on the free end thereof with a continuous groove 17 having a square cross-section, and another sealing ring 18 is inserted in this groove for sealing the plunger 3 against the housing 4.

These sealing rings 16 and 18 provide for sealing the product chamber 2 against the product outlet 29 in any position of the plunger 3, so that no connection exists between the product chamber 2 and the product outlet 29, whichever is the position of the plunger 3. The plunger 3 is driven by means of a usual compressed-air cylinder system 19. This compressed-air cylinder system 19, of which the construction is well-known in the art, consists of a compressed-air cylinder 20 which is supplied with compressed air via a compressed-air connector 21 and has a piston rod 22 that can be extended and retracted by means of compressed air. Control of the compressed-air cylinder 20 is effected through a 5-2-directional control valve 23 that can be operated by means of a handle 24.

FIG. 1 shows the home position of the apparatus 1 in which the sample chamber 12 is positioned in the region of the bore 14. In this position, the sample chamber 12 is constantly traversed by the flowing medium contained in the product chamber 2. In this position, compressed air is acting on the compressed-air cylinder 20 on the piston-side. If a sample of product is to be collected now from the product chamber 2, compressed-air is applied to the annular space of the compressed-air cylinder 20, whereby the piston rod 22 telescopes into the compressed-air cylinder 20 according to FIG. 2. As a consequence, the plunger 3 is moved within the housing 4 in such a manner that the sample chamber 12 reaches the region of the product outlet 29. For collecting the sample of product a cup holder 25 is mounted to the product outlet 29, by means of a bayonet catch not further shown in the drawing. Said cup holder consists of two U-shaped brackets pivotally connected to each other by their mutually facing legs. Said cup holder 25 holds a non returnable cup 26 for collecting the sample of product.

After the lapse of a predetermined time, within which the retracted sample of product has flown from the sample chamber 12 into the non returnable cup 26, the plunger 3 is returned to its home position according to FIG. 1 in which the sample chamber 12 is again positioned within the product chamber 2.

Accordingly, the above-described apparatus 1 has as a core piece a pneumatically operated plunger 3 with a product chamber 12 having a volume of e.g. 12 ml.

In the home position shown in FIG. 1, said sample chamber 12 is positioned within the product chamber 2 and hence in the product, so that it is permanently traversed by the flowing medium and therefore guarantees the collection of a representative sample of product. By the axial displacement of the plunger 3 by means of the pneumatic cylinder 20 the sample chamber 12 reaches a position above the product outlet 29 where the product gravimetrically runs out into the non returnable cup 26.

The sealing of the plunger 3 against the housing 4 is effected in the closed condition, i.e. with the plunger projected into the product chamber 2, by means of the metallic annular sealing gap between the plunger 3 and the housing 4, on one side and by means of a valve seat and ultimately a sealing ring 16, on the other side. In the opened condition, i.e. the position of the plunger 3 as shown in FIG. 2, sealing is effected through the sealing ring 16.

Since there is no connection between the product chamber 2 and the product outlet 29 at any time, the apparatus according to the invention is absolutely pressure-proof and vacuum-proof up to 10 bar. During the process of sampling sealing is effected through the metallic annular sealing gap between the plunger 3 and the housing 4. In the case of thin-bodied media such as solvents or the like which are under high pressure, sealing is effected additionally by the sealing ring 18 on the free end of the plunger 3.

The compressed-air cylinder 20 is controlled in the usual manner via a 5-2-directional valve and the handle 24. However, as an alternative electromagnetic control at predetermined intervals may be provided. Beyond, said compressed-air cylinder 20 can be equipped with a limit position monitoring system, so that the exact time of the sample collection can be put down e.g. by a process control system.

Supplementary, a pressure reservoir may be provided, so that the plunger 3 can be maintained in its home position as shown in FIG. 1 in case of a loss of compressed air. In the absence of such a pressure reservoir the plunger 3 will move to the position as shown in FIG. 2 if compressed air is lost. But even if this should happen any connection between the product outlet 29 and the product chamber 2 cannot be established, thanks to the sealing rings 16 and 18 that are provided, resulting in that in case of a loss of compressed air an amount of product which at maximum corresponds to the content of the sample chamber 12 would escape only once.

The apparatus according to the invention is particularly suited for products of low to medium viscosity which gravimetrically run out at the product outlet 29. Furthermore, the apparatus 1 is suited for temperatures up to 300° C. and for a pressure reaching from vacuum up to 10 bar. Chemraz or optionally Kalrez turned out as particularly advantageous as materials for the sealing rings 16 and 18, since these materials are chemically resistant to almost all products.

What is claimed is:

1. An apparatus for extracting a sample of a liquid or a gas product from a product chamber, comprising a sample chamber which is arranged in a housing or movement between a position projected into the product chamber and a position extracted from the product chamber, said housing being connected to a lateral side of the product chamber such as to surround an opening thereof in a sealing relation and having a product outlet as well as a plunger, the latter including said sample chamber and being supported for axial movement within said housing which is configured as a cylinder, characterized in that during normal operation said sample chamber is in a position projected into the product chamber and is movable toward the region of the product outlet only for collecting a sample of product, and that the plunger is sealed against the housing between the product outlet and the end of the housing protruding into the product chamber by means of a sealing ring and that said sealing ring is inserted in a recess in the lateral side of said housing.

2. The apparatus of claim 1, characterized in that said housing includes a recess in the region of the sample chamber in the projected position thereof.

3. The apparatus of claim 2, characterized in that said recess is formed as a bore, of which the diameter is slightly smaller than the length of the sample chamber.

4. The apparatus of claim 1, characterized in that the plunger has a plunger sealing ring on a free end in the region of the sample chamber.

5. The apparatus of claim 4, characterized in that the plunge sealing ring is inserted in a recess in the plunger.

6. The apparatus of claim 4 wherein the plunger sealing ring is an O-ring.

7. The apparatus of claim 1, characterized in that the product outlet has detachably mounted to it a cup holder for receiving non returnable cups.

8. The apparatus of claim 7, characterized in that said product outlet and said cup holder can be connected to each other by means of a bayonet catch.

9. The apparatus of claim 4 wherein the sealing ring is O-ring.

10. An apparatus for extracting a sample of product from a product chamber, comprising;
    a sample chamber;
    a housing in which the product chamber is arranged;
    wherein the sample chamber can be moved between a position projected into the product chamber and a position extracted from the product chamber;
    wherein the housing is connected to a lateral side of the product chamber such as to surround an opening thereof in a sealing relation;
    wherein the housing comprises:
      a product outlet;
      a plunger,
        wherein the plunger comprises the sample chamber and is supported for axial movement within the housing, which is configured to a cylinder and recess wherein a sealing ring is inserted in said recess in the lateral side of said housing and further wherein the housing includes a recess in the sample chamber in the projected position thereof.

11. The apparatus of claim 10, characterized in that the recess is formed as a bore, of which the diameter is slightly smaller than the length of the sample chamber.

12. The apparatus of claim 11, wherein the plunger has a plunger sealing ring on a free end of the sample chamber.

13. The apparatus of claim 12, wherein the plunger sealing ring is inserted in a recess in the plunger.

14. The apparatus of claim 12 wherein the plunger sealing ring is an O-ring.

15. The apparatus of claim 10, wherein the product outlet has a detachably mounted cup holder for receiving non returnable cups.

16. The apparatus of claim 15, wherein the product outlet and the cup holder can be connected to each other by means of a bayonet catch.

17. The apparatus of claim 10 wherein the sealing ring is an O-ring.

* * * * *